(12) United States Patent
Waagen (10) Patent No.: US 11,534,054 B2
(45) Date of Patent: Dec. 27, 2022

(54) VENT ASSEMBLY

(71) Applicant: KARL STORZ Endovision, Inc., Charlton, MA (US)

(72) Inventor: Tyrel Waagen, Sturbridge, MA (US)

(73) Assignee: KARL STORZ Endovision, Inc., Charlton, MA (US)

( * ) Notice: Subject to any disclaimer, the term of this patent is extended or adjusted under 35 U.S.C. 154(b) by 108 days.

(21) Appl. No.: 16/900,147

(22) Filed: Jun. 12, 2020

(65) Prior Publication Data
US 2021/0386275 A1    Dec. 16, 2021

(51) Int. Cl.
*A61B 1/00* (2006.01)
*A61B 1/12* (2006.01)
*A61B 1/015* (2006.01)

(52) U.S. Cl.
CPC ...... *A61B 1/00137* (2013.01); *A61B 1/00057* (2013.01); *A61B 1/015* (2013.01); *A61B 1/125* (2013.01)

(58) Field of Classification Search
CPC .......... F16K 17/18; F16K 17/19; F16K 17/196
See application file for complete search history.

(56) References Cited

U.S. PATENT DOCUMENTS

| | | | |
|---|---|---|---|
| 4,538,593 A * | 9/1985 | Ishii | A61B 1/00057 600/132 |
| 5,343,854 A * | 9/1994 | Katsurada | A61B 1/00068 600/146 |
| 5,634,880 A | 6/1997 | Feldman | |
| 10,335,017 B2 | 7/2019 | Waagen | |
| 2003/0150492 A1 * | 8/2003 | Sato | F16K 17/196 137/493.6 |
| 2015/0014567 A1 * | 1/2015 | Furuta | A61B 1/00068 251/324 |
| 2016/0302649 A1 * | 10/2016 | Nakajima | A61B 1/121 |
| 2016/0309990 A1 * | 10/2016 | Yajima | A61B 1/00114 |
| 2017/0100026 A1 * | 4/2017 | Inoue | B08B 3/08 |
| 2017/0138493 A1 * | 5/2017 | Yamaguchi | F16K 15/026 |
| 2020/0000329 A1 * | 1/2020 | Sugaya | A61B 1/015 |
| 2020/0159004 A1 * | 5/2020 | Iwanami | G01M 3/26 |
| 2020/0378527 A1 * | 12/2020 | Stephan | F16K 39/024 |

* cited by examiner

*Primary Examiner* — Michael J Carey
*Assistant Examiner* — Stephen Floyd London
(74) *Attorney, Agent, or Firm* — David Villalpando; Honigman LLP (57) ABSTRACT

A vent assembly configured to maintain predetermined positive and negative pressure differentials between gas within a compartment and the environment, such as a compartment defining an interior of an endoscope is provided. The vent assembly includes a first housing having an upper vent and a lower vent coupled to the compartment. A piston is movable from a closed position to a first position, and from the closed position to a second position. In the closed position the piston blocks the upper and lower vents. A positive pressure differential moves the piston so as to open the vent to allow gas to escape from the compartment. A negative pressure differential draws the piston from the closed position to a second position to allow gas to enter the compartment.

20 Claims, 5 Drawing Sheets

VENT ASSEMBLY

TECHNICAL FIELD

The disclosure relates to a vent assembly. In particular, the disclosure relates to a self-regulating vent assembly configured to regulate a pressure differential between a compartment and the environment.

BACKGROUND

Instruments such as endoscopes define an interior volume which is sealed during normal operation in order to, among other things, protect sensitive internal components of the instrument. Maintaining a seal to the interior volume during normal operation of the instrument also simplifies cleaning and sterilizing the instrument after use.

Although the instrument remains sealed in normal operation, there are circumstances in which it is desirable to temporarily break the seal to the interior volume. For example, in the case of air transport it is desirable to break the seal to the interior volume of the instrument in order to prevent a potentially damaging positive pressure differential between the interior volume of the instrument and the relatively lower pressure of the atmosphere inside the aircraft at high altitude. A positive pressure differential applied to an endoscope, for example, may cause elastic expansion in flexible sheathing material associated with the probe of the instrument. This expansion may result in elastic fatigue which eventually damages the material and may ultimately cause the material to rupture.

In the case of cleaning or sterilization, a sealed instrument may be subjected to conditions which produce both positive and negative pressure differentials between the interior volume of the instrument and the atmosphere in which the instrument is located. Positive pressure differentials during cleaning or sterilization pose the same threat noted above in relation to air transport. Negative pressure differentials may also damage certain components of the instrument.

Accordingly, it remains desirable to have a vent assembly that is used to maintain predetermined positive and negative pressure differentials between the interior of a compartment and the atmospheric pressure of the environment so as to allow the vent to open or close as a result of a change in environmental pressure.

SUMMARY

In one aspect a vent assembly for use with a compartment is provided. The vent assembly is configured to be self-regulating. The vent assembly opens to the environment in response to a positive or negative pressure differential between the compartment and the environment.

The vent assembly includes a first housing. The first housing includes an upper vent and a lower vent. The lower vent is fluidly coupled to a compartment. The vent assembly further includes a piston. The piston includes a first end and a carrier. The piston is movable from a closed position to a first position and is also movable from the closed position to a second position.

In the closed position, the first end blocks the upper vent and the carrier blocks the lower vent so as to seal the compartment from the environment. A positive pressure differential between the compartment and the environment that is greater than a first pressure differential moves the piston from the closed position to the first position. As the piston moves, the first end of the piston is displaced away from the compartment and opens the upper vent and the lower vent to allow pressure to escape from the compartment.

The piston is further movable from the closed position to the second position wherein a negative pressure differential that is greater in magnitude than a second pressure differential draws the piston from the closed position to the second position. As the piston moves, the first end is displaced towards the compartment so as to introduce pressure from the environment into the compartment. Accordingly, the piston is movable between the first and second positions so as to maintain the predetermined pressure differentials.

In one aspect, the positive pressure differential is a first pressure differential and the negative pressure differential is a second pressure differential wherein the first pressure differential is 500 mmHg and the second pressure differential is 310 mmHg. In another example, the first pressure differential may be 310 mmHg and the second pressure differential may be 120 mmHg. In yet another aspect the first and the second pressure differential may be the same and 760 mmHg or less, for example the first and second pressure differentials may be between approximately 120 mmHg and 700 mmHg.

In another aspect, the vent assembly may include a first biasing member and a second biasing member. The first biasing member may be disposed between a first surface of the carrier and an interior wall of the first housing. The first biasing member may have a compressive force that is greater than a compressive force of the second biasing member, thus making it easier to draw the piston towards the compartment relative to pushing the piston away from the compartment. In one aspect of the disclosure, the first biasing member and the second biasing member are wave springs.

The vent assembly may include a carrier gasket that is disposed on the carrier and movable between the first position and the second position. The vent assembly may further include a first gasket that is fixedly mounted to an opening of the upper vent. The carrier gasket and the first gasket are resilient members which are configured to form a seal.

The piston may be shaped so as to have features which close the upper and lower vents. In one aspect, the first end of the piston includes an indent that extends radially along an outer circumferential surface of the piston so as to define a bulbous end. The bulbous end is configured to engage the first gasket in a closed position so as to close the upper vent. The inner wall of the first housing may include a rib that extends radially along the inner wall of the first housing wherein the carrier gasket engages the rib in the closed position so as to close the lower vent.

In one aspect the vent assembly includes a leak testing device. The leak testing device includes a second housing. The second housing is configured to be seated onto the first housing. The second housing may include a connector disposed on a top wall of the second housing.

A connector pin is disposed within the second housing and a through hole fluidly connects an open top of the connector to an open end of the connector pin so as to allow fluids to be drawn from or delivered into the vent assembly. The connector pin is configured to engage the piston so as to move the piston into the second position.

In another aspect of the disclosure an endoscope having an outlet fluidly coupled to a compartment is provided. The endoscope includes a vent assembly. The vent assembly is configured to be self-regulating. The vent assembly opens to the environment in response to a positive or negative pressure differential between the compartment and the environment.

The vent assembly includes a first housing having an upper vent, a lower vent and a coupling member. The coupling member is configured to fluidly gauge the outlet. A piston is disposed within the first housing. The piston includes a first end and a carrier.

The piston is movable from a closed position to a first position and is also movable from the closed position to a second position. In the closed position, the first end blocks the upper vent and the carrier blocks the lower vent. The piston is movable from the closed position to the first position by a positive pressure differential between the compartment and the environment that is greater in magnitude than the first pressure differential. The first pressure differential is greater than the compressive force of the first biasing member so as to displace the first end of the piston away from the compartment and open the upper vent and the lower vent to allow the pressure to escape from the compartment.

The piston is movable from the closed position to the second position by a negative pressure differential that is greater in magnitude than a second pressure differential. The second pressure differential is greater than a compressive force of the second biasing member wherein the second pressure differential draws the piston from the closed position to the second position so as to displace the first end towards the compartment and introduce pressure into the compartment.

Accordingly, the endoscope includes a self-regulating vent assembly which allows for the compartment to maintain a range of pressures between predetermined positive and negative pressure differentials.

BRIEF DESCRIPTION OF THE DRAWINGS

The embodiment set forth in the drawings are illustrative and exemplary in nature and not intended to limit the subject matter defined by the claims. The following description of the illustrative embodiments can be understood when read in conjunction with the following drawings where like structure is indicated with like reference numerals and in which:

DETAILED DESCRIPTION OF PREFERRED EMBODIMENTS

Implementations herein are directed towards a vent assembly and an endoscope with a vent assembly. The vent assembly is configured to be self-regulating. The vent assembly opens to the environment in response to a positive or negative pressure differential between the compartment and the environment. As used herein, a positive pressure differential refers to a situation where the pressure within the compartment is greater than the environmental pressure. A negative pressure differential refers to a situation where the pressure within the compartment is less than the environmental pressure.

The vent assembly includes a piston that is movable from a closed position to a first position and from the closed position to a second position. The piston is disposed within a housing having an upper vent and a lower vent wherein a positive pressure differential greater in magnitude than a first pressure differential moves the piston from the closed position to the first position so as to displace a first end of the piston away from the compartment and open the upper vent and lower vent so as to allow pressure to be released from the compartment. A negative pressure differential that is a greater in magnitude than a second pressure differential draws the piston from the closed position to the second position so as to displace the first end towards the compartment and introduce pressure into the compartment. As such, the piston is movable between the first and second positions so as to maintain predetermined pressure differentials and eliminate the need for a user to insert a cap onto the compartment prior to shipment through air.

Figure 1:
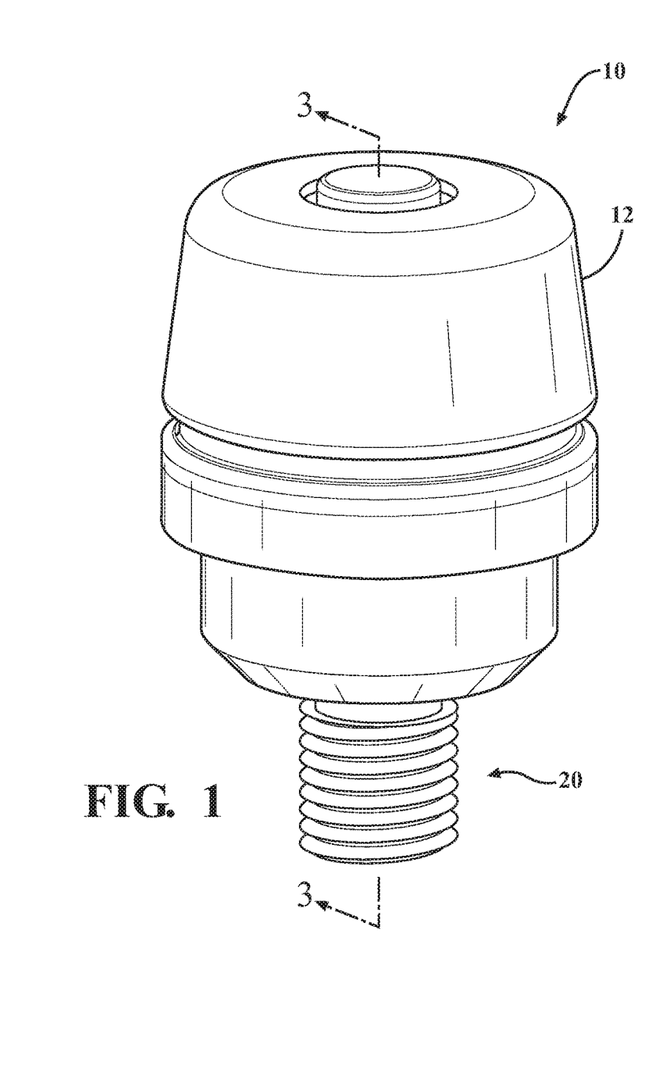
FIG. 1 is a prospective view of a vent assembly according to one or more embodiments illustratively described herein.

With reference first to FIG. 1, a schematic depiction of an illustrative embodiment of a vent assembly 10 is shown. The vent assembly 10 includes a first housing 12. The first housing 12 is a generally cylindrical shaped body. The first housing 12 may be formed of a durable and rigid material, illustratively including stainless steel.

A piston 14 is disposed within the first housing 12. The piston 14 includes a first end 16 and a carrier 18. The piston 14 is a generally elongated cylindrical member formed of a rigid and durable material, illustratively including stainless steel.

The first housing 12 includes a coupling member 20 configured to provide a fluid seal with a device 100 having a compartment 102, any device 100 with a compartment 102 currently known or used may be adapted for use herein, illustratively including a housing of a flexible endoscope 100 as shown in FIGS. 3-5, 7 and 8. A description of the vent assembly 10 is made herein in the context of an endoscope 100, but it should be appreciated that the vent assembly 10 may be used in other devices such as camera heads which couple with rigid optical endoscopes. For illustrative purposes, the coupling member 20 is shown as a threaded end. It should be appreciated that the endoscope 100 is modified to include a threaded bore which is open to the compartment 102 so as to provide a fluid path between the vent assembly 10 and the compartment 102 of the endoscope 100.

Figure 2:
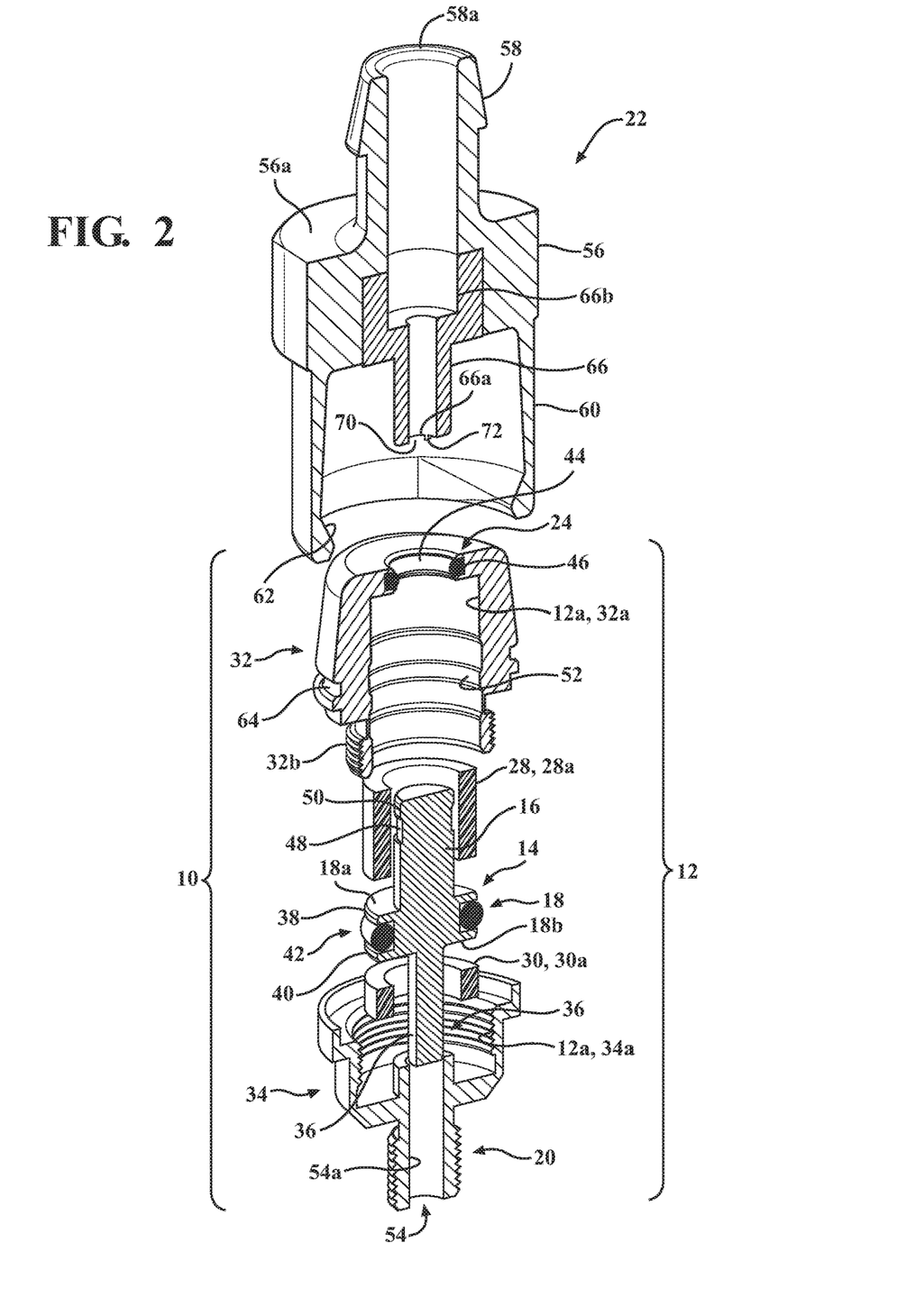
FIG. 2 is cross-sectional and exploded view of the vent assembly shown in FIG. 1 taken along line 3-3.

With reference now to FIG. 2. A cross sectional view of the vent assembly 10 is provided. FIG. 2 also provides a cross sectional view of a leak testing device 22. A description of the leak testing device 22 is provided below.

Figure 3:
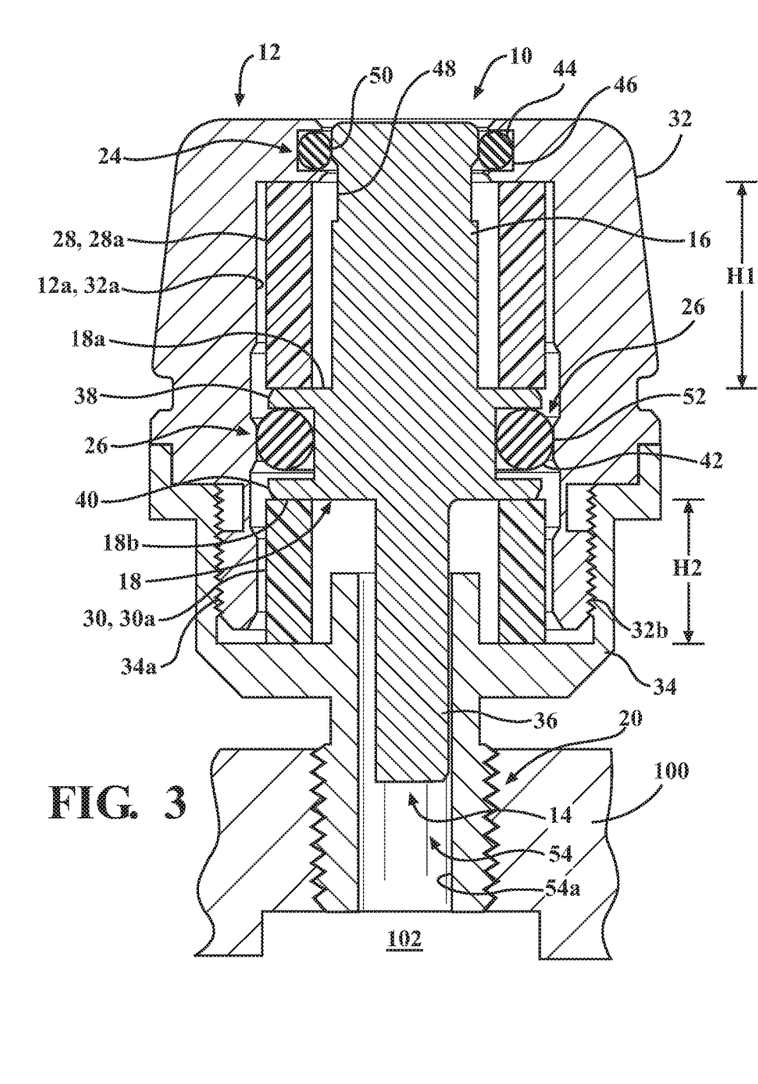
FIG. 3 is a cross sectional view of FIG. 1 taken along line 3-3 showing the piston in a closed position.
Figure 4:
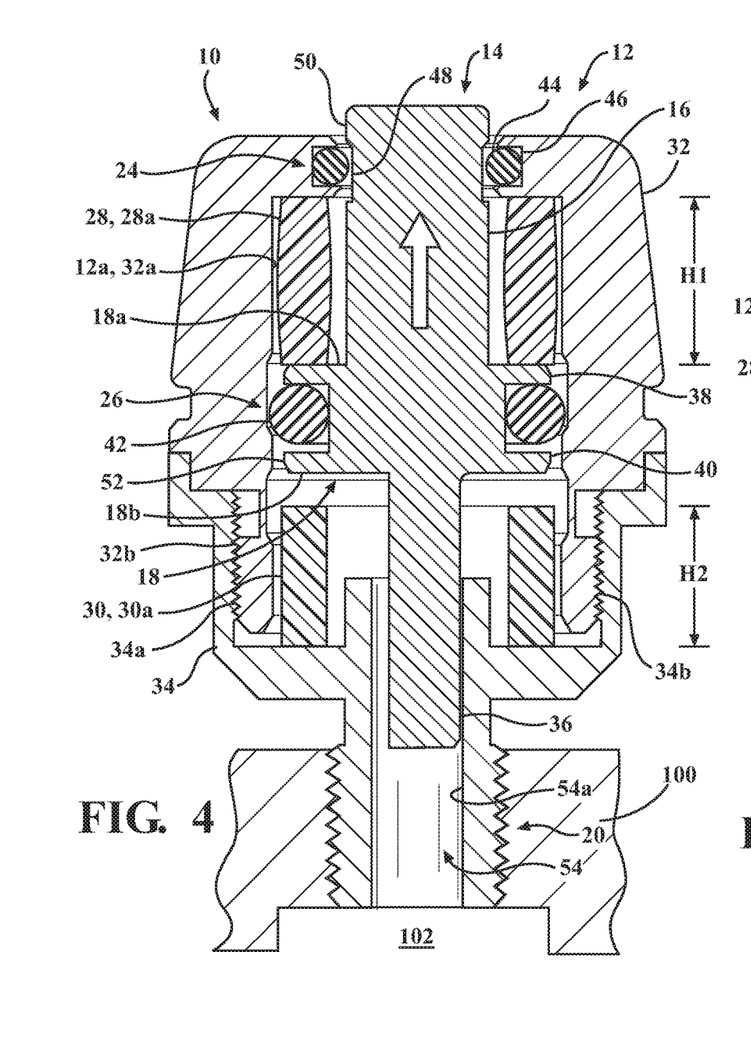
FIG. 4 is a view of FIG. 3 showing the piston in the first position.
Figure 5:
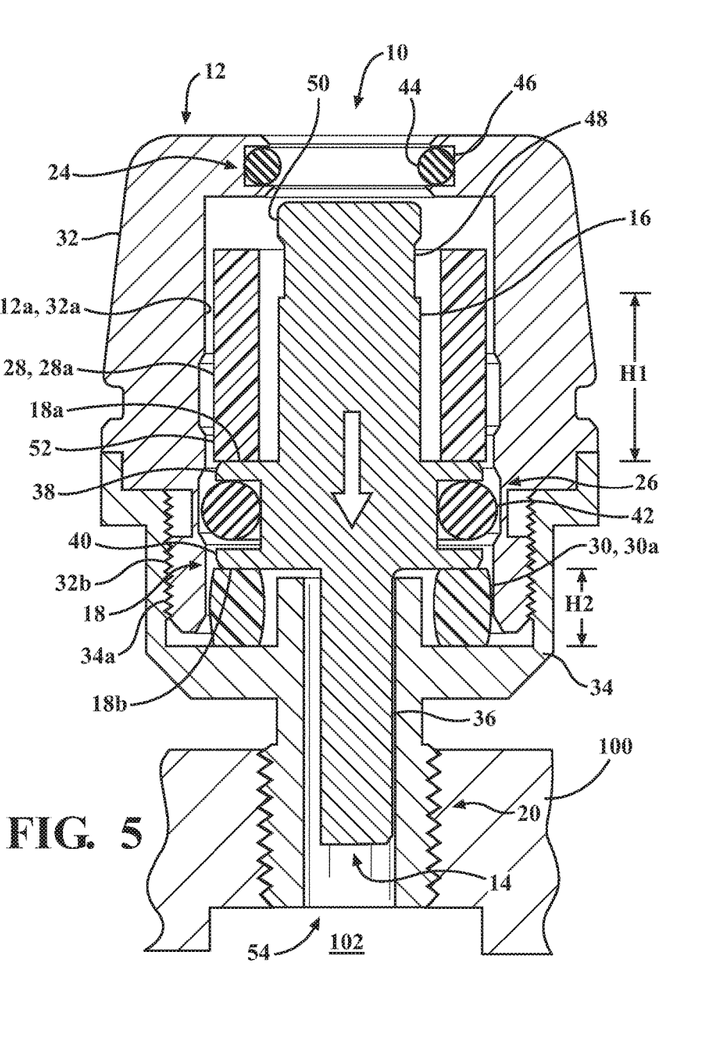
FIG. 5 is a view of FIG. 3 showing the piston in the second position.

With reference also to FIGS. 3-5, the first housing 12 includes an upper vent 24 and a lower vent 26. The upper vent 24 and the lower vent 26 define a path for which fluid, such as air, may pass. The lower vent 26 is in fluid communication with the coupling member 20 so as to provide a path for pressure to escape or be introduced into the compartment 102 as described in further detail below.

The piston 14 is movable from a closed position to a first position. A depiction of the closed position is provided in FIG. 3 and a depiction of the first position is provided in FIG. 4. The piston 14 is also movable from the closed position to a second position. A depiction of the second position is shown in FIG. 5.

With reference now to FIG. 3, in the closed position, the first end 16 of the piston 14 blocks the upper vent 24 and the carrier 18 blocks the lower vent 26. When the compartment 102 experiences a positive pressure differential that is greater in magnitude than a first pressure differential, the piston 14 is pushed away from the compartment 102 from the closed position to the first position, as depicted in FIG. 4. In the first position, the first end 16 of the piston 14 is displaced away from the compartment 102 and the upper vent 24 and the lower vent 26 are opened so as to allow pressure to escape from the compartment 102. When enough pressure is released to reduce the magnitude of the pressure differential to less than the first pressure differential, the piston 14 is moved back from the first position to the closed position.

When the compartment 102 experiences a negative pressure differential that is greater in magnitude than a second pressure differential, the piston 14 is drawn towards the compartment 102 from the closed position to the second position as shown in FIG. 5. In the second position, the piston 14 is displaced so as to allow pressure to be introduced from the upper vent 24 through the lower vent 26 into the compartment 102. When enough pressure is introduced into the compartment 102 to reduce the magnitude of the pressure differential to less than the second pressure differential, the piston 14 is moved back to the closed position.

In one aspect of the vent assembly 10, the vent assembly 10 may further include a first biasing member 28 and a second biasing member 30. The first biasing member 28 and the second biasing member 30 are configured to retain the piston 14 in a closed position, wherein a predetermined positive or negative pressure differential between the compartment 102 and the environment overcomes the compressive force of the first biasing member 28 and the second biasing member 30 so as to move the piston from the closed position to the first position or the second position as the case may be.

The first biasing member 28 may be disposed between a first surface 18a of the carrier 18 and an inner wall 12a of the first housing 12. The second biasing member 30 may be disposed between a second surface 18b of the carrier 18 and the inner wall 12a of the first housing 12. In a neutral state, such as when there is insignificant or no pressure differential, the first biasing member 28 and the second biasing member 30 position the piston 14 in the closed position. Both biasing members may be under a small amount of compression in the closed position to prevent unwanted movement and noise or to reduce the distance the piston must travel to vent.

The first housing 12 may include an upper housing 32 and a lower housing 34 which are fluidly coupled together so as to seal the inner space of the first housing 12 from the environment. The upper housing 32 has an upper inner wall 32a having a generally constant radius. The upper vent 24 is disposed on a top portion of the upper housing 32. The upper vent 24 is an opening that is concentric to the first end 16 of the piston 14. A bottom portion of the upper housing 32 may include a threaded outer surface 32b which is configured to threadingly engage a threaded inner wall 34a of the lower housing 34.

As shown the first biasing member 28 may be an upper wave spring 28a and the second biasing member 30 may be a lower wave spring 30a. The upper and lower wave springs 28a, 30a may be formed of the same material and the compression force of the upper and lower wave springs 28a, 30a may be determined by the amount of compression and the spring constant of the wave spring. The upper wave spring 28a and the lower wave springs 30a are generally porous so as to allow for air to pass through.

As shown in FIGS. 2-5 the upper wave spring 28a and the lower wave spring 30a have generally the same radial thickness. The upper wave spring 28a is longer than the lower wave spring 30a so as to have a similar spring constant despite being required to vent at a higher pressure differential. This allows for precise tuning of the positive venting pressure differential. This assumes that both the upper and lower wave springs 28a, 30a are formed of the same material. The upper and lower wave springs 28a, 30a are formed of a compressive material having a resilient nature, any such material currently known or later developed may be modified for use herein, illustratively including carbon steel, stainless steel, beryllium copper and the like. As used herein, the term compressive force refers to the amount of force that is necessary to compress the first or second biasing members 28, 30 a specified distance.

For illustrative purposes, the first and second biasing members 28, 30 are shown as being wave springs having the same thickness and formed of the same material. However, it should be appreciated that the dimensions of the first and second biasing members 28, 30 may differ so as to generate a desired compressive force. This may be done by adjusting the dimensions of the wave spring such as length or the spring constant. It should further be appreciated that the use of a wave spring is provided for illustrative purposes only and that other biasing mechanisms currently known or later developed may be adapted for use herein without limiting the scope of the appended claims. For instance, a helical spring or a leaf spring may be used so and may be tuned to have predetermined compression forces for use herein.

The first end 16 of the piston includes a diameter which is generally larger than a second end 36 on the opposite side of the piston. The first end 16 is generally a rod-shaped cylinder and the second end 36 is a rod-shaped cylinder having the generally uniform outer surface. The carrier 18 is disposed between the first end 16 and the second end 36.

The carrier 18 includes a first annular lip 38 that is spaced apart from a second annular lip 40 wherein a carrier gasket 42 is disposed between the first annular lip 38 and the second annular lip 40. The carrier gasket 42 may be formed of a resilient member such as a silicone. The carrier gasket 42 is a generally ring-shaped member seated within the space between the first annular lip 38 and the second annular lip 40.

A first gasket 44 is configured to seal the upper vent 24. In particular, the first gasket 44 is disposed within an annular indent 46 disposed on the top surface of the first housing 12 which defines the upper vent 24. The first gasket 44 may be formed of a resilient member such as a silicone. The first gasket 44 is a generally ring-shaped member seated within annular indent 46.

The first end 16 of the piston 14 may further include an upper indent 48 extending radially along an outer circumferential surface of the first end 16 so as to define a bulbous end 50. The bulbous end 50 is configured to engage the first gasket 44 in the closed position so as to close the upper vent 24.

The inner wall of the upper housing 32 of the first housing 12 may further include a rib 52 which extends radially along the upper inner wall 32a and above the threaded outer surface 32b of the upper housing 32. The carrier gasket 42 is configured to engage the rib 52 in the closed position so as to close the lower vent 26.

With reference now to FIG. 3, a depiction of the vent assembly 10 in the closed position is provided. In the closed position, the piston 14 is configured to form a closed seal with respect to the upper vent 24 and the lower vent 26. The bulbous end 50 of the piston 14 is pressed against an inner surface of the first gasket 44 and the outer surface of the first gasket 44 is in contact with the inner wall defining the annular indent 46. Thus, fluids such as air are not allowed to escape.

In the closed position the carrier gasket 42 is shown held within the space defined by the first and second annular lips 38, 40. The outer surface of the carrier gasket 42 is engaged with the rib 52 of the first housing 12 so as to provide a sealed engagement closing the lower vent 26. In the closed position, the first biasing member 28 and the second biasing member 30 are in an equilibrium state or a natural state holding the first gasket 44 and the carrier gasket 42 in a sealed engagement with the respective upper vent 24 and lower vent 26.

The lower housing 34 of the first housing 12 is connected to the compartment 102 of the device. The second end 36 of the piston 14 is seated within an outlet 54 of the lower housing 34. The second end 36 of the piston 14 is spaced apart from the inner wall 54a of the outlet 54 so as to allow fluids to pass.

With reference now to FIG. 4, the vent assembly 10 is shown as having moved from the closed position to the first position as indicated by the arrow. The first position is a position in which the piston 14 is displaced upward relative to the first housing 12 so as to be further away from the first compartment 102 relative to the closed position. This is attributed to a positive pressure differential between the compartment 102 and the environment. The positive pressure differential is greater than the compressive force of the first biasing member 28. In particular, the positive pressure differential is the first pressure differential that is greater than the compressive force of the first biasing member 28.

As the first biasing member is compressed, the carrier 18 holds the carrier gasket 42 and moves the carrier gasket 42 up and away from the rib 52. FIG. 4 shows that outer surface of the carrier gasket 42 is spaced apart from an inner wall 12a of the upper housing 32 so as to allow fluids to pass. The bulbous end 50 of the first end 16 of the piston 14 is moved upwardly and away from the first gasket 44 wherein the indent is opposite of the inner surface of the first gasket 44 so as to define a passage for which air is allowed to escape.

It should be noted that the height "H1" of the first biasing member 28 shown in FIG. 4 is shorter than the height "H1" of the first biasing member 28 shown in FIG. 3, which indicates that the first biasing member 28 is compressed. Additionally, the height "H2" of the second biasing member 30 has reached a maximum value as the piston 14 is moved from the closed position to the first position such that the second biasing member 30 is no longer in contact with the surface 18b of the carrier 18.

With reference now to FIG. 5, the vent assembly 10 is shown in the second position. The pressure in the compartment 102 is less than the environment, creating a vacuum. The vacuum is sufficient to draw the piston 14 into and towards the compartment 102 as indicated by the arrow. In other words, the negative pressure differential that is greater in magnitude than the second pressure differential is sufficient to overcome the compressive force of the second biasing member 30.

FIG. 5 shows that the height "H2" of the second biasing member 30 in the second position is shorter than the height "H2" of the second biasing member 30 in the closed position as shown in FIG. 3 which indicates that the second biasing member has been compressed. The height "H1" of the first biasing member 28 remains the same as the piston 14 is moved from the closed position to the second position such that the first biasing member 28 is no longer in contact with the inner wall 12a of the upper housing 32.

As the piston 14 is moved from the closed position to the second position, the carrier 18 holds the carrier gasket 42 in position between the first and second annular lips 38, 40 so as to move the carrier gasket 42 down and away from the rib 52. FIG. 5 shows a final state of the second position wherein the outer surface of the carrier gasket 42 is spaced apart from an inner wall of the upper housing 32 so as to define a path for which fluids may escape or in this case may be introduced.

Concurrently, the first end 16 is moved downwardly so that the bulbous end 50 is below the first gasket 44 so as to allow for pressure to be introduced into the compartment 102. It should be appreciated that the wave springs are not a solid mass and are generally porous. Accordingly, gas may be passed through the wave springs itself, thus wave springs do not inhibit the introduction of pressure into the compartment 102.

With reference again to FIGS. 3, 4 and 5, a description of the operation of the vent assembly 10 is provided. For use herein, the vent assembly 10 is shown coupled to an endoscope 100, however, it should be appreciated that other devices may benefit from the use of the vent assembly 10 described herein and that the use of an endoscope 100 is not limiting to the scope of the appended claims. The vent assembly 10 may be used with any device 100 that is subject to a change in atmospheric pressure. Such a change may occur during the course of air shipment.

The vent assembly 10 is a self-regulating vent which opens to the environment based upon a pressure differential between the compartment 102 of the endoscope 100 and the environment. The pressure differential may be a positive pressure differential or a negative pressure differential.

The piston 14 is configured to move from a closed position to the first position when the positive pressure differential is greater in magnitude than the first pressure differential. The piston 14 is configured to move from a closed position to the second position when the negative pressure differential is greater in magnitude than the second pressure differential. As such, the vent assembly 10 is movable from the closed position wherein the vent assembly 10 is sealed from the environment to the first or second position wherein the vent assembly 10 is configured to allow pressure to escape or to introduce pressure into the compartment 102 as described in greater detail below. It should be appreciated the first and second biasing members 28, 30 may be configured to allow movement of the piston 14 based upon any predetermined first and second pressure differential between the compartment and the environment necessary to prevent damage to components such as seals, sheathing, and others that may be sensitive to expansion, elastic fatigue, etc. In one aspect, the first pressure differential is 500 mmHg and the second pressure differential is 310 mmHg. In yet another example, the first pressure differential may be 310 mmHg and the second pressure differential may be 120 mmHg. In yet another aspect the first and the second pressure differential may be the same, for example the first and second pressure differentials may be 760 mmHg or less.

In most cases, the pressure differentials fall within a range between approximately 120 mmHg and 700 mmHg.

In FIG. 3 the vent assembly 10 is shown in the closed position. In the sealed position neither the first biasing member 28 nor the second biasing member 30 are compressed or if so, only a small amount as noted above. As such, the bulbous end 50 of the piston 14 is engaged with the first gasket 44 so as to close off the upper vent 24 and the carrier gasket 42 is engaged with the rib 52 so as to close off the lower vent 26.

With reference now to FIG. 4, the piston 14 is moved from the closed position to the first position. This may be a result of an altitude change. For example, the vent assembly 10 may be transported via air from sea level to a cruising altitude. At a cruising altitude the pressure differential between the compartment 102 and the environment is greater than 310 mmHG which causes an outward pressure relative to the compartment 102. The 310 mmHG of pressure is sufficient to overcome the compressive force of the first biasing member 28, compressing the first biasing member 28.

As the first biasing member 28 is compressed, the piston 14 is moved from the closed position to the first position wherein the first end 16 is moved away from the first gasket 44 so as to create a space between the annular indent 46 of the piston 14 and the inner surface of the first gasket 44. Concurrently, the carrier 18 moves the carrier gasket 42 away from engagement with the rib 52 providing a space between the outer surface of the first gasket 44 and the inner wall 12a of the upper housing 32. Thus, internal pressures from the compartment 102 is released until the pressure is less than 310 mmHG wherein the first biasing member 28 is able to return to its natural state as shown in FIG. 3.

The expansion of the first biasing member 28 moves the piston 14 into the closed position. This may produce a vacuum inside the compartment 102 when the vent assembly 10 is placed back in atmospheric pressure at or nearer to sea level. If the vacuum is greater than the second pressure differential, e.g. 120 mmHG, the vacuum overcomes the compressive force of the second biasing member 30 carrying the piston 14 towards the compartment 102 as shown in FIG. 5. In the second position, the first biasing member 28 is compressed and shorter relative to the closed position.

The first biasing member 28 remains in a natural position and the carrier 18 moves the carrier gasket 42 away from the rib 52 creating a path between an outer circumferential surface of the carrier gasket 42 and the inner wall 12a of the first housing 12 and the bulbous end 50 of the piston 14 is below and displaced away from the first gasket 44 thus allowing air to be introduced into the compartment 102 until the negative pressure differential is less than 120 mmHg.

Figures 6, 7:
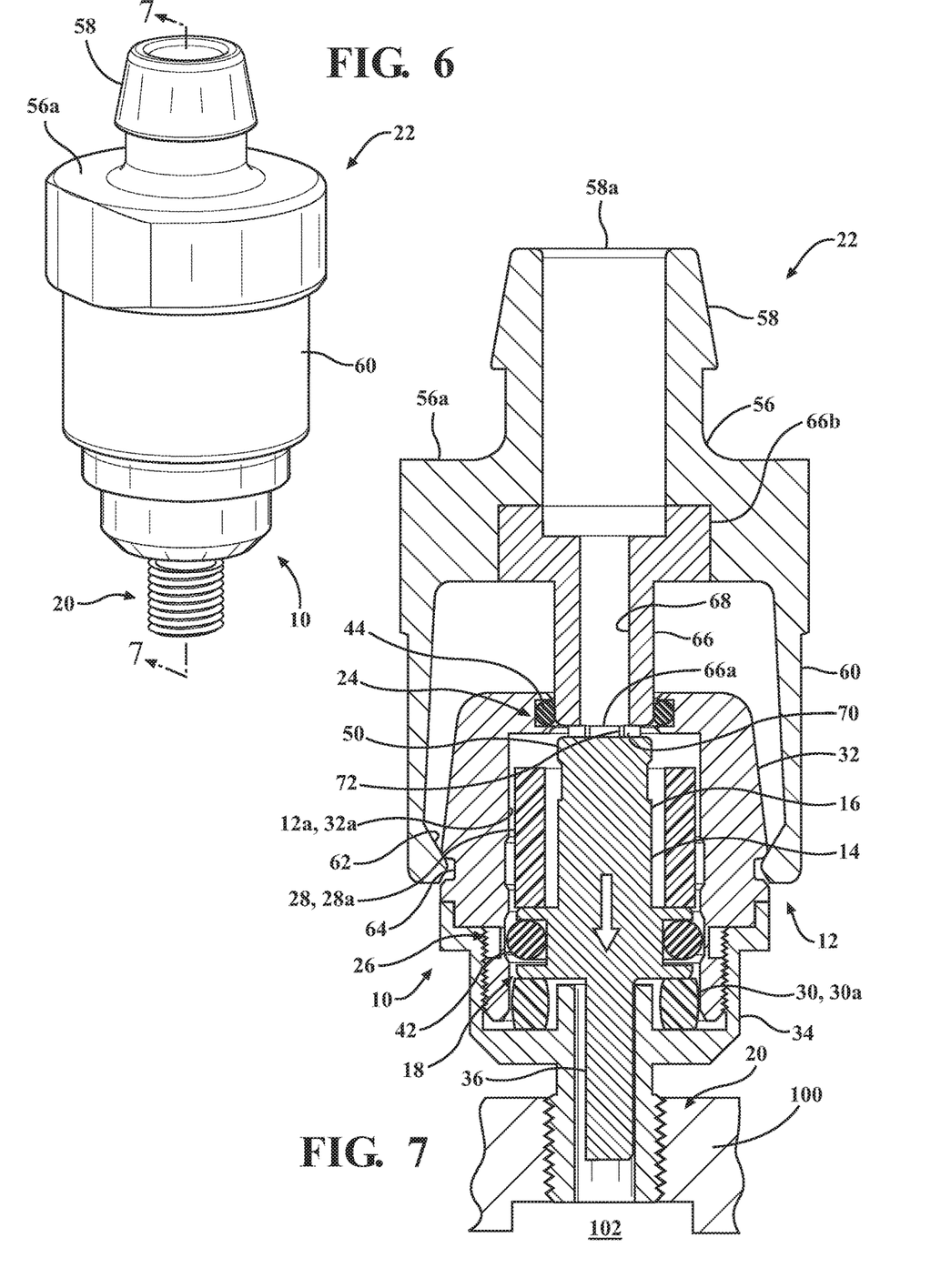
FIG. 6 is a prospective view showing a leak testing device mounted onto the vent assembly.
FIG. 7 is a cross sectional view of FIG. 6 taken along line 7-7.
Figure 8:
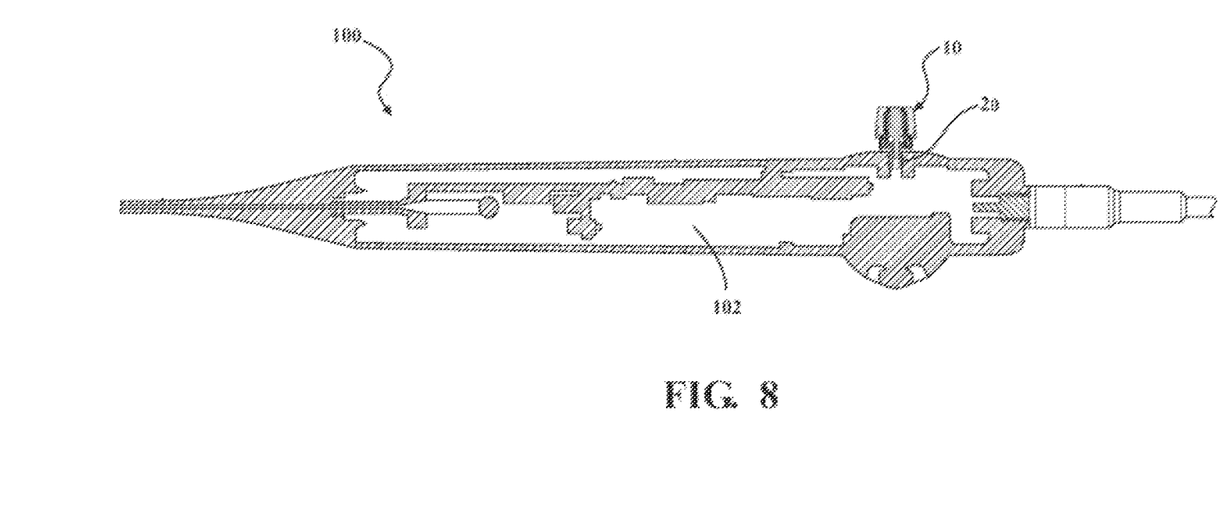
FIG. 8 is a prospective view showing the vent assembly mounted to an endoscope.

With reference again to FIG. 2 and now to FIG. 6, in one aspect of the disclosure the vent assembly 10 may further include a leak testing device 22. The leak testing device 22 is configured to be mounted on top of the upper housing 32. The leak testing device 22 is further configured to be coupled to a pneumatic source so as to perform a leak test.

The leak testing device 22 includes a second housing 56. The second housing 56 is configured to be seated onto the first housing 12 and includes a connector 58 disposed on a top wall 56a of the second housing 56. The connector 58 includes an open top 58a to allow for the introduction of air into the vent assembly 10. The connector 58 may be barbed so as to help retain an engagement with a tube (not shown) which is fluidly coupled to a pneumatic source (not shown).

With reference now to FIG. 7, a cross sectional view of FIG. 6 taken along 7-7 is provided. As shown, the second housing 56 includes a generally cylindrical space defined by a circumferential lower wall 60. The distal end of the second housing 56 may include an inner rib 62 disposed on an inner surface of the circumferential lower wall 60. The second housing 56 may be formed of a pliable and resilient material such as a polypropylene and is configured to flex over the outer surface of the first housing 12 wherein the inner rib 62 is configured to be seated into a circumferential groove 64 on the outer surface of the first housing 12.

The leak testing device 22 includes a connector pin 66. The connector pin 66 is fixedly mounted to a connector pin housing 66b. The connector pin 66 is a generally long tubular member having a through-hole 68 that extends between an open end 66a of the connector pin 66 and the open top 58a of the connector 58 so as to provide a fluid communication between the open top 58a of the connector 58 and the open end 66a of the connector pin 66. The open end 66a of the connector pin 66 includes a plurality of cut outs 70 which allow for the passage of air. In particular, a pair of adjacent cut outs 70 define a leg 72. As shown in FIG. 7, the distal end of the leg 72 is pressed against the piston 14 and the cut out defines a space in which air may enter or exit the through-hole 68 of the connector pin 66.

The connector pin 66 has a length dimensioned to engage the piston 14 so as to move the piston 14 from a closed position to the second position when the second housing 56 is mounted onto the first housing 12 as shown in FIG. 7. Thus, the bulbous end 50 of the piston 14 is displaced away from the first gasket 44 and the carrier gasket 42 is displaced from the rib 52 so as to form a fluid path from the distal end of the connector pin 66 to the interior of the vent assembly 10.

Accordingly, the leak testing device 22 provides for a simple means for conducting a leak test. In particular, the leak testing device 22 is a singular device which is simply mounted onto the upper vent 24 housing of the vent assembly 10 and allows for a connection to a pneumatic pump to conduct leak testing.

A number of implementations have been described. Nevertheless, it will be understood that various modifications may be made without departing from the spirit and scope of the disclosure. Accordingly, other implementations are within the scope of the following claims.

I claim:

1. A vent assembly configured to self-regulate a pressure differential between a volume within a compartment and an environment, the vent assembly comprising:
   a first housing including an upper vent and a lower vent, coupled to the compartment;
   a piston having a first end and a carrier, the piston movable from a closed position to a first position, and movable from the closed position to a second position, wherein in the closed position, the first end blocks the upper vent and the carrier blocks the lower vent;
   a first biasing member operably engaged with a first surface of the carrier; and
   a second biasing member spaced apart from the first biasing member, and operably engaged with a second surface of the carrier, the second surface opposite the first surface,
   wherein a positive pressure differential that is greater in magnitude than a first pressure differential, moves the piston from the closed position to the first position displacing the first end of the piston away from the compartment, opening the upper vent and the lower vent to allow gas to escape from the compartment, wherein a negative pressure differential that is greater in magnitude than a second pressure differential, moves the piston from the closed position to the second position displacing the first end of the piston towards the compartment, opening the upper vent and the lower vent to allow gas to enter into the compartment, and the first biasing member and the second biasing engaging the respective first surface and second surface of the carrier so as to retain the piston in the closed position when the positive pressure differential is less than the first pressure differential and the negative pressure differential is less than the second pressure differential.

2. The vent assembly as set forth in claim 1, wherein the first pressure differential is between 120 mmHg and 760 mmHg and the second pressure differential is between 120 mmHg and 760 mmHg.

3. The vent assembly as set forth in claim 1, wherein the first biasing member is disposed between the first surface of the carrier and an inner wall of the first housing.

4. The vent assembly as set forth in claim 3, wherein the second biasing member is disposed between the second surface of the carrier and the inner wall of the first housing.

5. The vent assembly as set forth in claim 4, wherein the first biasing member has a compressive force that is greater than a compressive force of the second biasing member.

6. The vent assembly as set forth in claim 4, wherein the first biasing member and the second biasing member are wave springs.

7. The vent assembly as set forth in claim 1, further including a carrier gasket, the carrier gasket disposed on the carrier.

8. The vent assembly as set forth in claim 7, further including a first gasket, the first gasket fixedly mounted to an opening of the upper vent.

9. The vent assembly as set forth in claim 8, wherein the carrier includes a first annular lip spaced apart from a second annular lip, the carrier gasket disposed between the first annular lip and the second annular lip.

10. The vent assembly as set forth in claim 9, wherein the first end of the piston includes an indent extending radially along an outer circumferential surface so as to define a bulbous end, the bulbous end engaging the first gasket in the closed position so as to close the upper vent, and wherein an inner wall of the first housing includes a rib extending radially along the inner wall, the carrier gasket engaging the rib in the closed position so as to close the lower vent.

11. The vent assembly as set forth in claim 1, further including a leak testing device, the leak testing device including a second housing, the second housing configured to be seated onto the first housing, the second housing including a connector disposed on a top wall of the second housing, the connector having an open top;

a pin disposed within the second housing, the pin having an open end; and a through-hole fluidly connecting the open top of the connector to the open end of the pin, the pin configured to engage the piston so as to move the piston into the second position.

12. An endoscope having an outlet fluidly coupled to a compartment, the endoscope comprising:

a vent assembly configured to maintain predetermined positive and negative pressure differentials between a gas within the compartment and an environment, the vent assembly including:

a first housing including an upper vent, a lower vent and a coupling member configured to fluidly engage the outlet;

a piston having a first end and a carrier, the piston movable from a closed position to a first position, and movable from the closed position to a second position, wherein in the closed position, the first end blocks the upper vent and the carrier blocks the lower vent;

a first biasing member operably engaged with a first surface of the carrier; and a second biasing member spaced apart from the first biasing member, and operably engaged with a second surface of the carrier, the second surface opposite the first surface, wherein a positive pressure differential that is greater in magnitude than a first pressure differential, moves the piston from the closed position to the first position displacing the first end of the piston away from the compartment and opening the upper vent and the lower vent to allow gas to escape from the compartment;

wherein a negative pressure differential that is greater in magnitude than a second pressure differential, moves the piston from the closed position to the second position displacing the first end towards the compartment to allow gas to enter into the compartment; and wherein the first biasing member and the second biasing member engage the respective first surface and second surface of the carrier so as to retain the piston in the closed position when the positive pressure differential is less than the first pressure differential and the negative pressure differential is less than the second differential.

13. The endoscope as set forth in claim 12, wherein the first pressure differential is between 120 mmHg and 760 mmHg and the second pressure differential is between 120 mmHg and 760 mmHg.

14. The endoscope as set forth in claim 12, wherein the first biasing member is disposed between the first surface of the carrier and an inner wall of the first housing.

15. The endoscope as set forth in claim 14, wherein the second biasing member is disposed between the second surface of the carrier and the inner wall of the first housing.

16. The endoscope as set forth in claim 15, wherein the first biasing member has a compressive force that is greater than a compressive force of the second biasing member.

17. The endoscope as set forth in claim 15, wherein the first biasing member and the second biasing member are wave springs.

18. The endoscope as set forth in claim 12, further including a carrier gasket, the carrier gasket disposed on the carrier.

19. The endoscope as set forth in claim 18, further including a first gasket, the first gasket fixedly mounted to an opening of the upper vent, wherein the carrier includes a first annular lip spaced apart from a second annular lip, the carrier gasket disposed between the first annular lip and the second annular lip.

20. The endoscope as set forth in claim 12, further including a leak testing device, the leak testing device including a second housing, the second housing configured to be seated onto the first housing, the second housing including a connector disposed on a top wall of the second housing, the connector having an open top, a pin disposed within the second housing, the pin having an open end, and a through-hole fluidly connecting the open top of the connector to the open end of the pin, the pin configured to engage the piston so as to move the piston into the second position.

\* \* \* \* \*